United States Patent [19]

Amidon et al.

[11] Patent Number: 5,569,452

[45] Date of Patent: Oct. 29, 1996

[54] PHARMACEUTICAL FORMULATION HAVING ENHANCED BILE ACID BINDING AFFINITY

[75] Inventors: Gordon L. Amidon; Lizbeth B. Sherman; John R. Crison, all of Ann Arbor, Mich.

[73] Assignee: TSRL, Inc., Ann Arbor, Mich.

[21] Appl. No.: 453,438

[22] Filed: May 30, 1995

Related U.S. Application Data

[63] Continuation of Ser. No. 115,414, Aug. 31, 1993, abandoned.

[51] Int. Cl.$^6$ ............................. A61K 31/74; B29C 49/00
[52] U.S. Cl. ............................................ 424/78.1; 424/528
[58] Field of Search ..................... 424/78.1, 528

[56] References Cited

U.S. PATENT DOCUMENTS 3,692,895   9/1972   Nelson et al. .......................... 424/78

FOREIGN PATENT DOCUMENTS 9305084   3/1993   WIPO .

OTHER PUBLICATIONS

Zhu et al., JMS–Pure Appl. Chem., A29(9), pp. 711–721, (1992).

Tan et al., "Studies on complexation between β–cyclodextrin and bile salts" Int. J.Pharm., 74:127–135 (1991).

De Simone et al., J. of Pharm. Sci., vol. 67, #12, Dec. 1978, pp. 1695–1697.

Benson et al., J. of Pharm. Sci., vol. 82, 1, (1993), pp. 80–89.

Benson et al., "In vitro studies to investigate the reasons for the low potency of cholestgramine & colestipol" J. Pharm. Sci., 1993, vol. 82, #1, pp. 80–86.

Antenucci et al., "Enzymatic Degradation of α– and β–Cyclodextrins . . ." J. Agric. Food. Chem., 32:1316–1321 (1984).

De Caprio et al., "Bile acid and sterol solubilization in 2-hydroxypropyl–β–cyclodextrin" J. Lipid.Res., 33:441–443 (1992).

Miyajima et al., "Interaction of β–Cyclodextin with Bile Salts in Aqueous Solutions" Chem. Pha,m.Bull., 34:1395–1398 (1986).

Szejtli, J. "Cyclodetrins in Drug Formulations: Part I" Pharmaceutical Technology, 24–38 (1991).

Primary Examiner—Nathan M. Nutter
Attorney, Agent, or Firm—Kohn & Associates

[57] ABSTRACT

A pharmaceutical formulation comprising a polymeric resin having bile acid binding properties in combination with at least one bile acid binding material which enhances the bile acid binding affinity and/or capacity of the formulation, methods for preparing the formulations and methods for using the formulations.

16 Claims, 5 Drawing Sheets

- ■ 0.1M CD IN POTASSIUM PHOSPHATE
- □ 0.25 CD IN POTASSIUM PHOSPHATE
- ◆ 0.1M CD IN ACETIC ACID
- ◇ 0.25M CD IN ACETIC ACID
- ▲ 0.1M CD IN WATER

- ■ NO VVR
- □ VVR BY PEG 1500
- ◆ VVR BY PEG 3350
- ◇ VVR BY DEXTRIN
- ▲ VVR BY PLURACARE F127

PHARMACEUTICAL FORMULATION HAVING ENHANCED BILE ACID BINDING AFFINITY

This is a continuation of application Ser. No. 08/115,414 filed on Aug. 31, 1993, and now abandoned.

FIELD OF INVENTION

The present invention provides pharmaceutical formulations useful in binding all common bile acids, conjugates, metabolites and related compounds such as cholic acid, glycocholate, taurocholate, chenodeoxycholic acid, glycochenodeoxycholate, taurochenodeoxycholate, deoxycholic acid, glycodeoxycholate, taurodeoxycholate, lithocholic acid, glycolithocholate, taurolithocholate, ursodeoxycholic acid and related compounds; and a method for using the formulations and methods for preparing the formulations.

BACKGROUND OF THE INVENTION

Studies have shown there to be a direct correlation between high serum-cholesterol levels and coronary heart disease. Cholesterol and triglycerides circulate in the plasma bound to proteins and are classified according to their density: very low-density lipoproteins (VLDL), low-density lipoproteins (LDL), or high-density lipoproteins (HDL). The HDL is the so-called "good" form of cholesterol, whereas the LDL is believed to be involved with the build-up of plaque in blood vessels.

Serum-cholesterol levels considered to be normal or acceptable vary with the age of individuals, but it is generally believed that levels in the range of 200 mg/dL are acceptable, meaning such an individual is not in a particularly high-risk category for coronary heart disease. Some reports indicate that nearly half the adults in the United States have concentrations of serum cholesterol that are above the optimal levels. Studies carried out in the 1980s also have shown that a reduction in the concentration of cholesterol-carrying lipoproteins can diminish the risk of heart disease.

Currently, known bile acid sequestering agents require large doses (colestipol 15–30 grams/day and cholestyramine 4–24 grams/day), and these agents cannot be administered in their dry form. The colestipol resin is available as a powder that is dispersed in water or a beverage (COLESTID). The cholestyramine is available in a flavored bar form (CHOLYBAR-Parke-Davis) and as a dispersible powder (QUESTRAN-Mead Johnson).[1]

Several drug therapies for reducing serum-cholesterol levels exist, including cholestyramine and colestipol, which are bile acid sequestering agents acting in the gastrointestinal tract and not absorbed into the body, as well as small molecules, such as dextrothyroxine sodium, clofibrate, probucol, gemfibrozil, and lovastatin which are absorbed into the body and act through altering the synthesis, metabolism and/or distribution of cholesterol in the body.

Cyclodextrins (CD) given orally have been shown to have lipid lowering activity and bile acid binding capabilities in vitro.[2,3,4] However, when β-CD is administered orally, insignificant amounts are absorbed throughout the gastrointestinal tract. Most of the cyclodextrin is metabolized by the microflora in the colon. The metabolites are further metabolized and are finally excreted as carbon dioxide and water.[5] This extensive digestive and metabolizing capability of the gastrointestinal tract also eliminates the effectiveness of other bile binding compounds such as proteins (e.g., albumin and antibodies) and lipids (such as triglycerides) when administered orally.

The present invention discloses an improved formulation which is useful in lowering serum-cholesterol levels; the formulation comprising a bile acid binding resin or bile acid sequestering agent in combination with one or more bile acid binding materials. The formulation of the present invention provides an improvement over the known bile acid sequestering agents in that the formulation of the present invention is much more efficient and stable in binding bile acids and thereby reducing the quantity of formulation that must be administered.

SUMMARY OF THE INVENTION

The present invention is comprised of a bile acid binding polymeric resin in combination with one or more bile acid binding materials (BBM). Any polymeric resin which binds bile acid can be used in the present formulation. Preferred resinous bile acid binding polymers include colestipol and cholestyramine. The BBM component of the present invention is a material which increases the binding affinity and/or capacity of the bile acid binding resin material and typically includes carbohydrates, lipids and proteins, including antibodies or antibody fragments to bile acids.

The present invention also provides a method for preparing the formulation of the present invention as described in detail herein below.

The present invention provides means for lowering serum-cholesterol levels in a patient in need thereof which comprises administering an improved bile acid binding resinous formulation.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

The polymeric resins which find use in the present invention are any such resins which bind or adsorb bile acids and related compounds which will diffuse into the resin and be held or physically retained in the resin in part by the bile binding material (BBM) incorporated into the resin. Many such resins are known in the art and include those which are commercially available such as colestipol and cholestyramine resin, amberlite and other ion exchange and non ion exchange resins. Other such resins are also described in the literature, including the microporous cholestyramine known as cholpor[6] and the anion exchange resin formed from 2-methylimidazol and dichlorohydrin[7]. It will be readily apparent to those skilled in the art that other such resins known in the art can be employed in practicing the present invention.

Figure 1A:
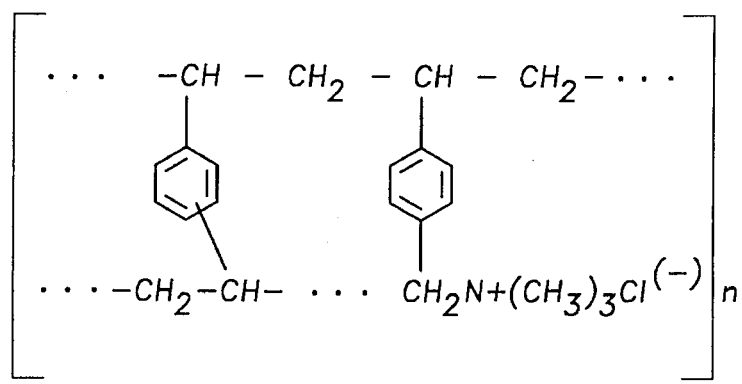
FIG. 1(A) shows the chemical structure of cholestyramine.

Cholestyramine and colestipol are the preferred bile acid binding resins in practicing the present invention. Cholestyramine resin, also known as DOWEX 1X2-Cl, is available commercially as QUESTRAN (Mead Johnson)[1] and has the structure shown in FIG. 1(A) hereof. Cholestyramine is prepared from chloromethyl styrene, divinylbenzene, and trimethylamine by procedures known in the art.[8]

Figure 1B:
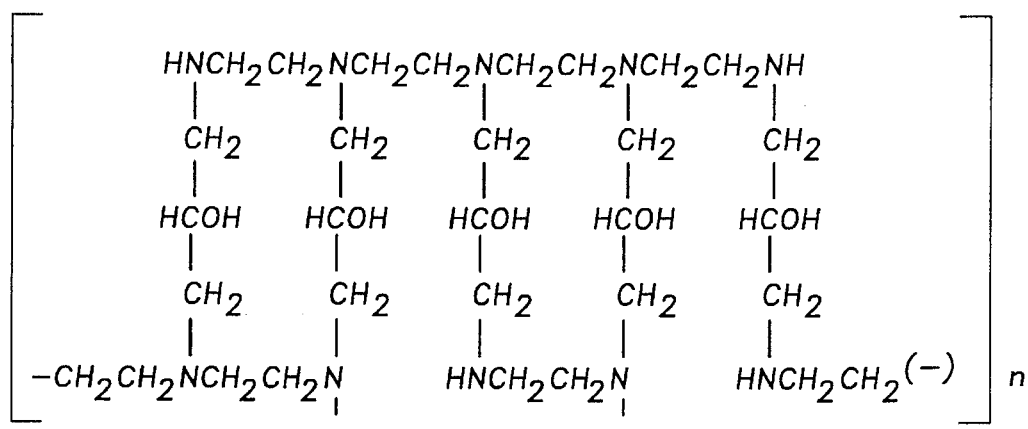
FIG. 1(B) shows the chemical structure of colestipol.

Colestipol is available as COLESTID (Upjohn) and has the structure shown in FIG. 1(B). The synthesis of colestipol is described in U.S. Pat. No. 3,692,895, and the patent is incorporated herein by reference thereto.

Bile acid binding resins are known to be effective in lowering plasma-cholesterol levels; and, inasmuch as they are not absorbed by the digestive system, such resins are considered to be safe and effective. The present invention provides that the bile acid binding resins can be modified to improve their ability to bind bile acids by incorporating into the resins materials that are known to have an affinity for bile acids. Such materials, in general, increase the bile acid binding of the resin, providing an improved formulation useful in treating patients having elevated levels of cholesterol. By increasing the affinity of the material for bile acids, less material is needed to achieve effective therapy.

The materials having bile acid binding ability used in the formulations of the present invention include carbohydrates, lipids and proteins, including antibodies or antibody fragments to bile acids. More particularly, the materials include carbohydrates having an affinity for bile acids such as carbohydrates from alfalfa, corn, wheat, and oats, and, in particular, include cyclodextrins.

There are numerous cyclodextrins which are useful in practicing the present invention. Cyclodextrins are cyclic carbohydrates consisting of 6, 7, or 8 glucose units and are called α, β, and γ-cyclodextrin, respectively. Cyclodextrins and derivative compounds have found wide applicability in the pharmaceutical industry.[9] Cyclodextrins, including heptakis (2,6-di-O-methyl)-β-cyclodextrin (DIMEB), are reported to have a strong affinity for cholesterol.

In addition to DIMEB, other cyclodextrins (CD) which are useful in the present invention include α-CD, β-CD, and γ-CD, and derivatives thereof, such as heptakis (2,3,6-tri-O-methyl)-β-CD; randomly methylated -β-CD; monosuccinyl-D/MEB; α-hydroxypropyl β-CD; a polymer of soluble β-CD cross-linked with epichlorohydrin and carboxymethyl groups containing the polymer dimethyl-β-CD, and trimethyl-β-CD. Hydroxypropyl-β-cyclodextrin is commercially available as Encapsin HPβ (Janssen Biotech N.V.). The use of α-hydroxypropyl-β-CD in the pharmaceutical industry is described by C. Strattan.[5]

Cyclodextrins are known to have an affinity for bile acids.[10] Cyclodextrins of particular interest in practicing the present invention are β-cyclodextrin and hydroxypropyl-β-cyclodextrin.

Proteins which are useful in the present invention have an affinity for bile acids. Examples of such proteins are bovine serum albumin, egg albumin, casein, $\alpha^1$-acid glycoprotein, gelatin, and soy, peanut, almond, and wheat vegetable proteins, as well as antibodies or antibody fragments to bile acids. Antibodies to bile acids are prepared by procedures generally known in the art.[11] Proteins from vegetable sources are fragmented using a variety of enzymes such as pepsin, trypsin, α-chymotrypsin, lactase, cellulase, elastase, amalyase, papain, etc. to prepare them for use and enhance their bile acid binding affinity.

The formulation of the present invention can be prepared by various methods. One method of preparation is a swelling/deswelling approach whereby the resin is permitted to swell in a liquid which contains bile acid binding material (BBM), then deswelling the resin with a second liquid, thereby entrapping the BBM within the resin. The liquid used to swell the resin preferably causes the resin to swell and expand to a greater degree than would occur under normal physiological conditions, thus creating space within the resin for entrapping the BBM. The liquid used to deswell the resin is one in which the BBM is substantially insoluble.

Various liquids or combinations of liquids are useful for swelling the resin, including water, lower alcohols (such as, methanol and ethanol), dimethyl formamide, acetone, water and sulfuric acid, water and propyleneglycol, water and dimethylsulfoxide, formamide, styrene, and various concentrations (from 20% to 95%) of styrene in either methanol or acetone. Also, polyethylene glycol, acetic acid, benzoic acid, oleic acid, lactic acid, and phosphoric acid can be used. Styrene and various combinations of styrene were found to be particularly useful in the swelling/deswelling void volume reduction described in further detail hereinbelow.

Figure 2:
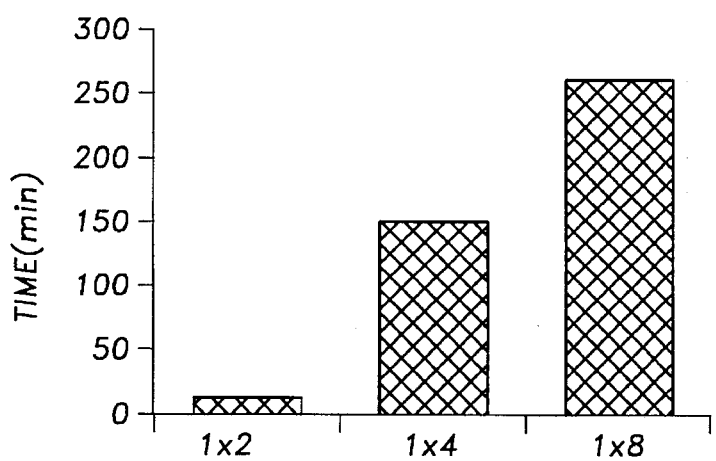
FIG. 2 is a graph showing time for 50% uptake of bile acid utilizing ultraviolet and heat-treated resins.

Using formamide to swell the resin wherein β-cyclodextrin is dispersed in the liquid, at a quantity of cyclodextrin per volume of liquid of 0.1M, a 43%, a 15%, and a 3% incorporation of cyclodextrin into DOWEX having a 1×2, a 1×4, and a 1×8 cross-linking ratio, respectively, was obtained. The rate of uptake of bile salt, e.g., salts of glycocholic acid and/or taurodeoxycholic acid, by these three resin formulations was measured and the results are shown in FIG. 2 hereof.

In another procedure for preparing the resin formulations, the void volume of the resins is reduced. The term void volume reduction as used herein means a reduction in the matrix space of the resin. The void volume reduction was accomplished by exposing the resin to ultraviolet (UV) or gamma radiation, the use of heat, and by the incorporation of monomers and catalysts and initiators.

Figure 3:
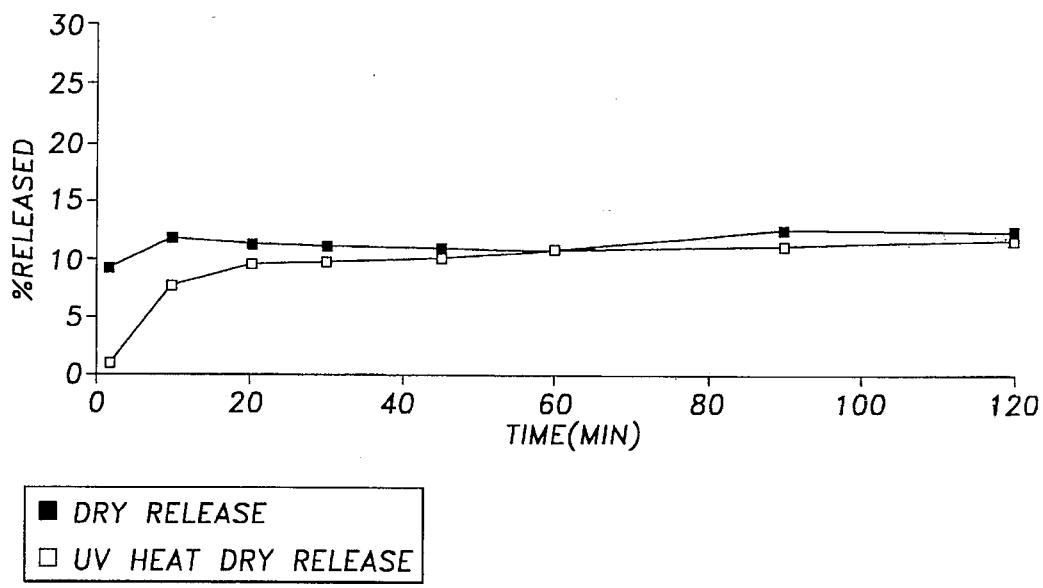
FIG. 3 shows results of the release of CD from a resin formulation described herein.

The effect of UV radiation and high temperature on a formulation of the present invention using Dowex® as the resin and cyclodextrin (CD) as the BBM was evaluated. The procedure for incorporating the BBM is the same as described previously. The procedure for measuring the rate of cyclodextrin release from the resin is set forth in Example 1 and the results are set forth in FIG. 3 hereof. As seen from FIG. 3, the UV and heat treated resin showed an 88% and 66% decrease in the amount of CD released at the 2 minute and 10 minute sampling points, respectively, compared to the control values taken at the same time points.

Both the control and the UV/heat treated resin seem to have similar loading concentrations of about 12%.

The effect on cross-linking by the addition of monomers to the formulation was evaluated by the procedure described in Example 2 thereof. Example 2(A) describes the preparation of a resin formulation wherein cyclodextrin and monomer (styrene) are added to DOWEX 1X2 simultaneously.

Figure 4:
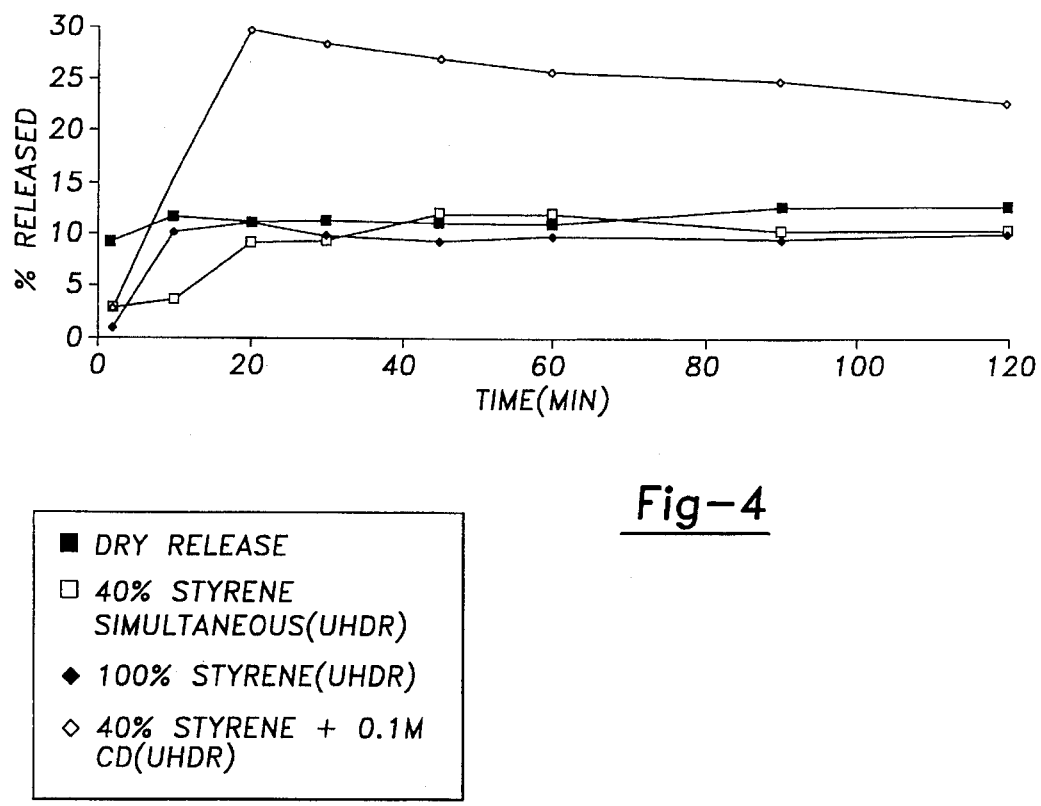
FIG. 4 shows results of the release of CD from the experiment set forth in Example 2B.

Example 2(B) describes the preparation of a resin formulation wherein the monomer is added subsequently to the addition of cyclodextrin to the DOWEX 1×2 resin. The results of these experiments are set forth in FIG. 4 wherein "U" means UV irradiation; "H" means heat; and "DR" means dry release. As seen from the graph in FIG. 4, the 100% styrene shows an 89% decrease and 14% decrease in the amount of CD released at the 2 minute and 10 minute sampling points, respectively. By adjusting these variables varous levels of entrapment and retention of BBM in the resins can be achieved.

The preferred method for preparing the resin formulation is by chemical synthesis of the resin with the incorporation of the BBM occurring during this synthesis.

The process used to prepare the DOWEX-type resins having an BBM, either β-CD or HP-β-CD, incorporated therein is substantially the same as described in the literature,[6] the procedure being illustrated in Example 3 herein.

The incorporation of hydroxypropyl-β-CD or β-CD into colestipol was investigated, which is a preferred resin for use in preparing the formulation of the present invention.

Similar procedures discussed above were utilized here for swelling and deswelling. It was also found that maintaining a slightly acidic pH facilitated the swelling process. Solvents of an acid nature that were found useful in swelling the resin include acetic, oxalic, malonic, formic, and propionic acids. Acetic acid was found to swell the resin better than the other solvents, e.g. 7.2 ml/gm in acetic acids acetic acid vs. 5.8 ml/gm in HCL. Other monocarboxylic acids had swelling characteristics similar to acetic acid and were better at swelling the resin than were the dicarboxylic acids. The procedure for incorporating the HP-β-CD into the colestipol is disclosed in Example 4(A). The rate of release was measured as described in Example 1 below. The results showing the effect the solvent used to swell the resin had on the release of HP-βCD is shown in FIG. 5.

Figure 5:
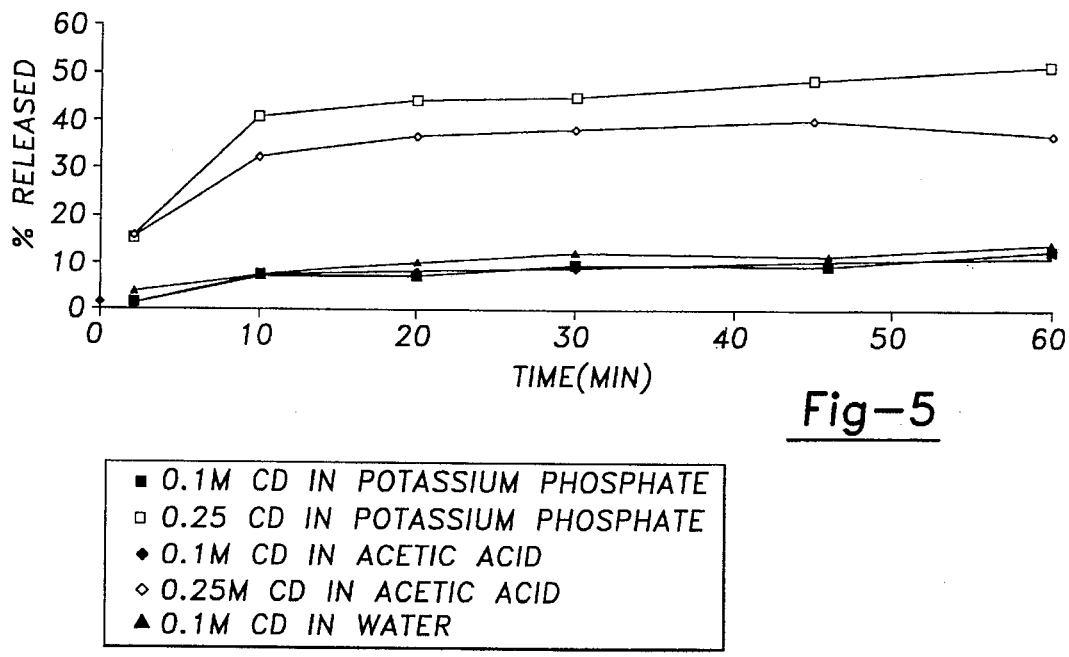
FIG. 5 is a graph showing the effect of swelling solvent on the CD release.

As can be seen from FIG. 5, the uptake of HP-βCD by colestipol is not dependent on the amount of swelling induced by the solvent:

4.84 gm/ml in water;

4.92 gm/ml in pH 6.5 potassium phosphate;

7.24 gm/ml in 1N acetic acid.

The uptake of HP-β-CD by colestipol is linearly dependent upon the concentration of HP-β-CD in the solution:

0.10M HP-β-CD—150 mg/gm complex;

0.25M HP-β-CD—500 mg/gm complex.

Figure 6:
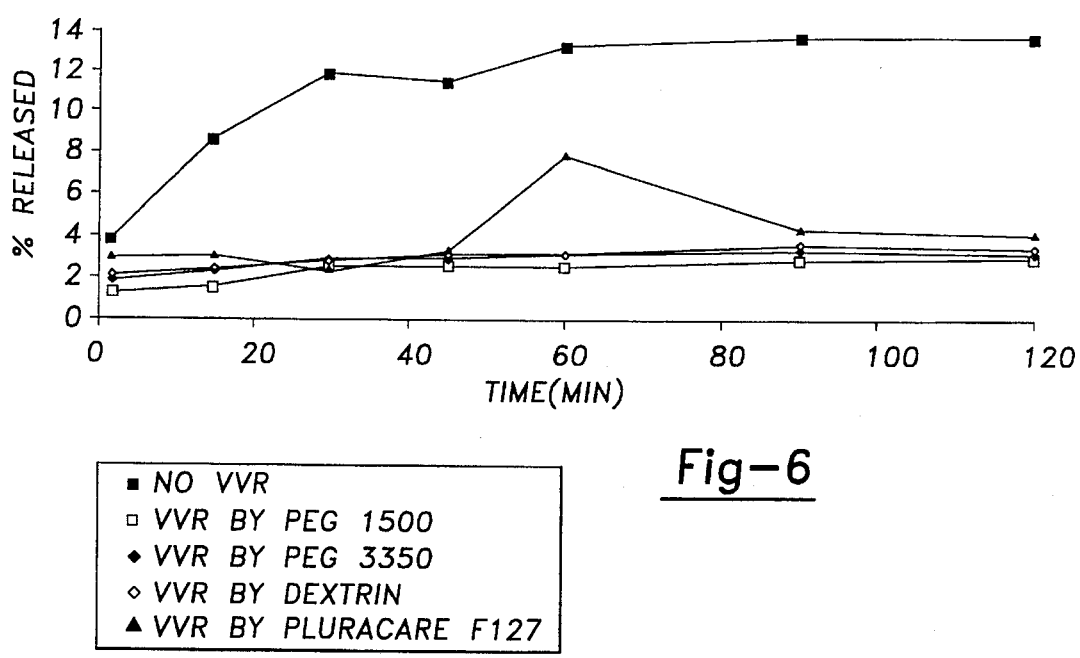
FIG. 6 is a graph showing the effects of void volume reduction of colestipol on the release rate of cyclodextrin.

Another procedure used for preparing the resin formulations is void volume reduction. The void volume reduction for colestipol was accomplished by incorporating the CD into the colestipol and then reducing the void volume through the use of polymers. Example 4(B) describes the preparation of the resin formulation. FIG. 6 shows the effect of the void volume reduction on the release of the CD from the formulation.

Figure 7:
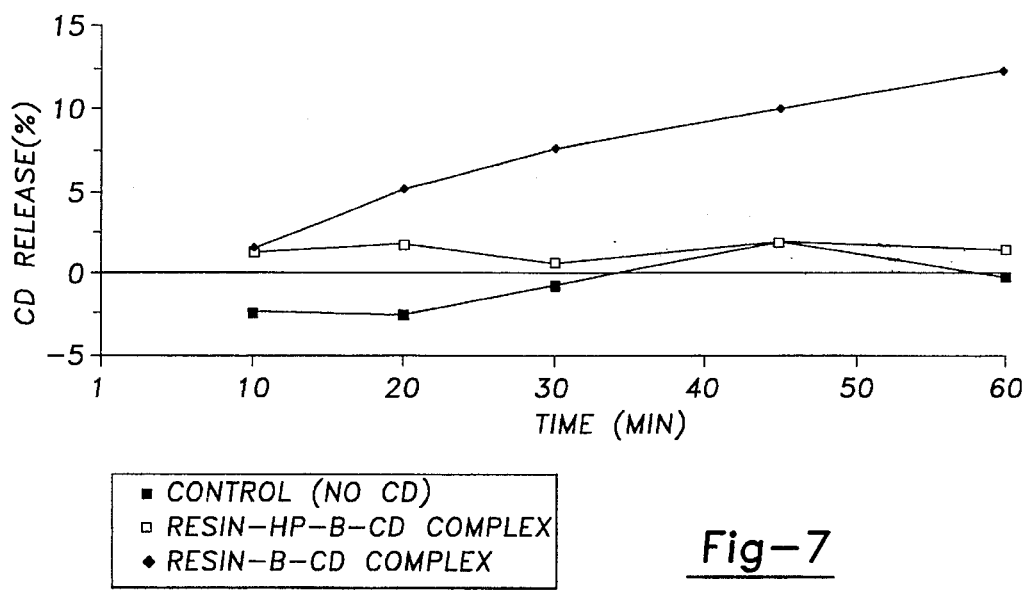
FIG. 7 is a graph showing the CD release over time for colestipol and modified colestipol formulation synthesized by procedure of Example 5, procedure 2.
Figure 8:
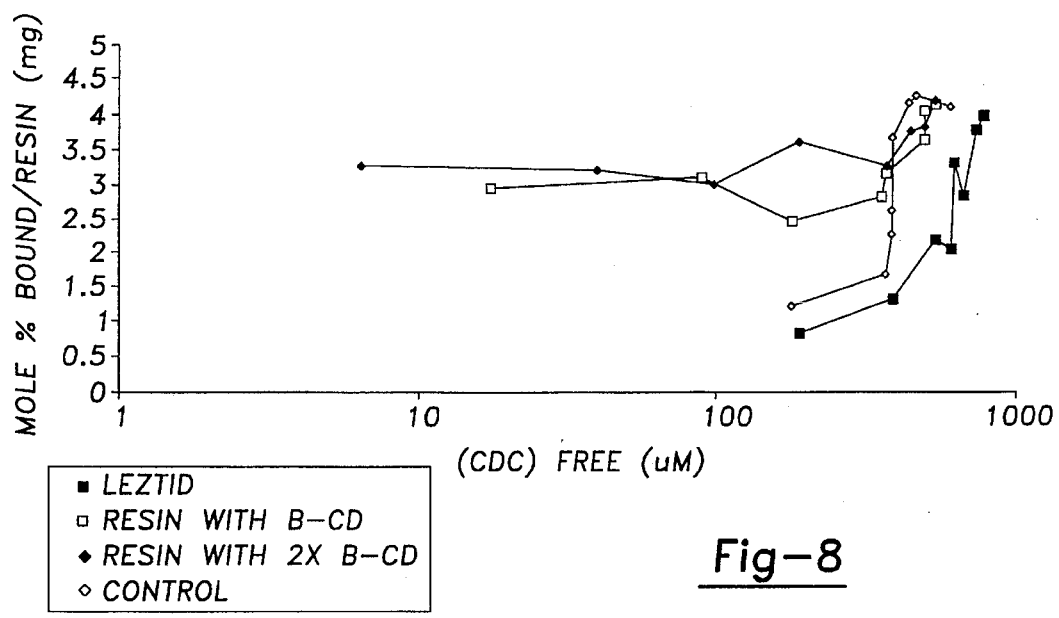
FIGS. 8 and 9 show the binding bile acids to the resin formulations, wherein the resin is synthesized by the procedure of Example 5, procedures 1–2, respectively.
Figure 9:
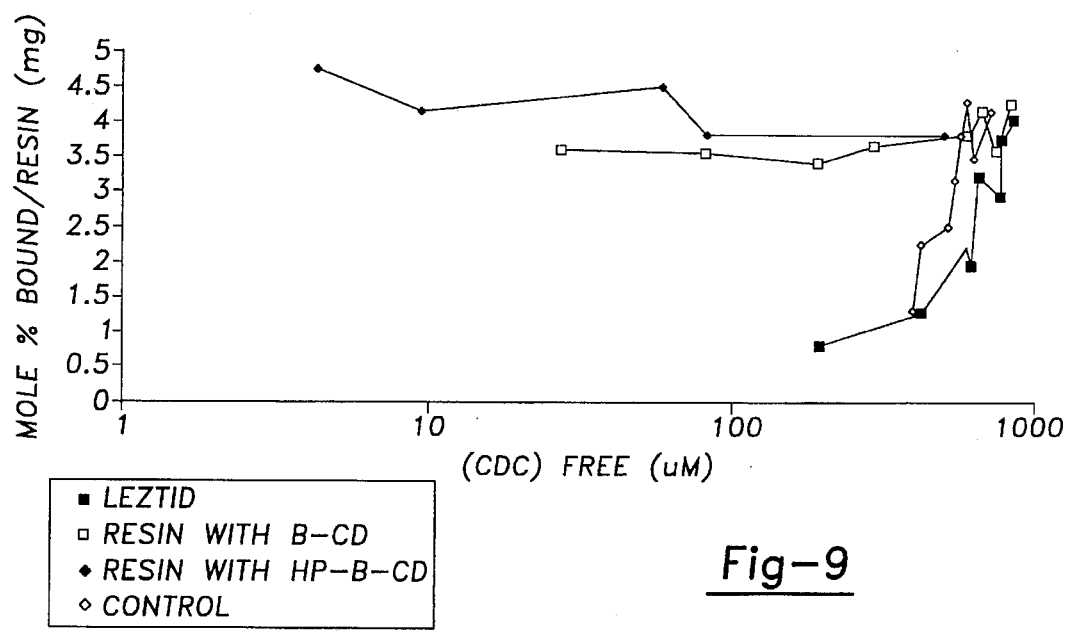

As stated above, the most preferred method for preparing the resin formulations of the present invention is chemical synthesis of the resin and incorporation of the BBM during the chemical synthesis. The general procedure for the synthesis of colestipol and related resins is set forth in U.S. Pat. No. 3,692,895. The process used to prepare colestipol-type resins having a BBM, either HP-β-CD or β-CD, incorporated therein is substantially the same as that described in the '895 patent, only the BBM is added. The basic procedure is set forth in Example 5. The quantities of components are indicated in Example 5. The resins prepared by these procedures were evaluated to determine the amount of cyclodextrin that was bound to the resin. Two procedures were used to characterize the resin-cyclodextrin formulation. The results are given in FIGS. 7–9. FIG. 7 shows the results of the release of any unbound cyclodextrin from the resin formulation. FIGS. 8 and 9 show the amount of bile acid binding to the resin formulation, in these figures COLESTID, which is also sold as LEXTID in Sweden, is the commercially available colestipol product and the bile acid used for the binding studies is chenodeoxycholate.

In using the resin formulations of the present invention to reduce plasma cholesterol levels in a patient, the formulations can be used in the same manner as cholestyramine and colestipol are used. The amount of resin formulation of the present invention will vary with each patient and the severity of the hypercholesterolemia of the patient. Typically, a patient would be given a quantity of the formulation of the present invention which is less than the recommended amounts of colestipol or cholestyramine for achieving a reduction in cholesterol levels. The superior bile binding properties of the present invention permit the administration of a lesser amount of resin formulation as compared to the resins presently available in the marketplace.

The following examples further illustrate the invention as described above.

EXAMPLE 1

Release of Cyclodextrin (CD) from Cholestyramine or Colestipol:

1. Weigh 50 mg of incorporated resin into a small vial.
2. Add 3 ml of water, stir.
3. Remove 0.03 ml at desired sampling points. Add to 0.97 ml of $Na_2CO_3$. Collect all time points.
4. Prepare a series of standards of CD in $Na_2CO_3$ from 0 to 500 μg.
5. Prepare a $6\times10^5$M solution of phenolphthalein (PHE) in $Na_2CO_3$ from a stock solution of 0.006M PHE in ethanol.
6. Add 1 ml of the PHE to each standard. Read at 550 nm.
7. Add 1 ml of the PHE to each sample. Read at 550 nm. Read all the samples together.

EXAMPLE 2(A)

Simultaneous Incorporation of Cyclodextrin and Monomer:

1. Prepare a 0.1M CD solution in 40% styrene/ethanol (v/v).
2. Add 10 ml of the CD solution from step 1 to every gram of cholestyramine used for incorporation.
3. Stir for 24 hours
4. Wash with acetone, ethanol and again with acetone.
5. Expose to UV radiation (9" at 360 nm) for 24 hours.
6. Expose to heat (125° C.) for 24 hours.
7. Store at 50% relative humidity for 24 hours.
8. Monitor the release following the procedure in Example 1.

EXAMPLE 2(B)

Incorporation of Monomer into a Cholestyramine/CD Formulation:

1. Using resin prepared as in Example 2A, add 10 ml of styrene to each 2 g of resin. Stir for 24 hours.
2. Wash with acetone.

3. Expose to UV radiation (9" at 360 nm) and heat 125° C.) for 24 hours, 48 hours, and 72 hours.
4. Store at 50% RH for 24 hours.
5. Monitor the release following the procedure in Example 1.

EXAMPLE 3

Cholestyramine with Cyclodextrin Synthesis:

Procedure I - Emulsion Synthesis

A. Polymerization
  1. Mix chloromethylstyrene, divinyl benzene and benzoyl peroxide together. Add cyclodextrin and stir.
  2. Dissolve emulsifying agent in water.
  3. Add the solution from step #2 to the material from step #1. Stir rapidly to form an emulsion.
  4. Heat to <90° C., continue stirring until polymerization is complete.
  5. Rinse with water, acetone and alcohol.
  6. Dry.
B. Amination.
  1. Swell the dry material from part A in toluene.
  2. Bubble in trimethylamine gas while stirring.
  3. Increase temperature to 85° C. Heat until reaction is complete.
  4. Rinse with water, acetone and alcohol.
  5. Dry.

Procedure II - Solid Synthesis

A. Polymerization
  1. Mix chlormethylstyrene, divinyl benzene and benzoyl peroxide together. Add cyclodextrin and stir.
  2. Increase temperature to <90° C. Continue stirring until polymerization is complete.
  3. Rinse with water, acetone and alcohol.
  4. Dry
B. Same as Procedure I Amounts of Materials Used:

| Material | Range (% of resin by weight) |
|---|---|
| Divinyl Benzene | 2%–8% |
| Styrene | 92%–98% |
| Benzoyl Peroxide | 0.2% |
| CD | 1%–10% |
| Water (for emulsion) | as needed |
| Ethyl Ether | as needed for swelling |
| Chloromethyl Ether | as needed for swelling |
| AlCl$_3$ | 10% |
| Toluene | as needed for swelling |
| Trimethylamine | as needed |

EXAMPLE 4(A)

Procedure for the Incorporation of CD into Colestipol:
1. Prepare a 0.1M CD solution in water.
2. Add 10 ml of the CD solution from step 1 to every gram of colestipol used for incorporation.
3. Stir for 24 hours.
4. Wash with acetone, ethanol and again with acetone.
5. Dry at 50° C. for 24 hours.
6. Monitor the release following the procedure in Example 1.

EXAMPLE 4(B)

Procedure for the Incorporation of Polymers into a Colestipol/CD Formulation
1. Using the resin prepared as in Example 6(A) add 10 ml of a 40% solution of one of the following polyethylene glycol (PEG) 1500, PEG 3500, Dextrin, Pluracare F127 to 1 gm of resin. 2. Allow to equilibrate 72 hours. 3. Wash with acetone, ethanol and again with acetone. 4. Dry at 50° C. for 24 hours. 5. Monitor the release following the procedure in Example 1.

EXAMPLE 5

Procedure For Synthesis of Colestipol With Cyclodextrin:

(A) Procedure 1

1. Add a suitable organic solvent, water, sodium salt of dodecylbenzenesulfonic acid, (SDBS), sodium hydroxide and the hydroxy propyl-β-CD or β-CD to a flask.
2. Begin heating to 80° C.
3. Add the epichlorohydrin (EPI) slowly.
4. Heat for 45 minutes.
5. Add the diethylenetriamine,
6. Add the EPI.
7. Continue heating.
8. Cool. Wash with water,
9. Wash with acetone, ethanol and water.
10. Dry.

(A) Procedure 2

1. Add a suitable organic solvent, water, sodium salt of dodecylbenzenesulfonic acid, (SDBS), sodium hydroxide, diethylenetriamine, and the HP-β-CD or β-CD to a flask.
2. Begin heating to 80° C. while stirring.
3. Add the epichlorohydrin (EPI) slowly.
4. Heat.
5. Cool. Wash with water.
6. Wash with acetone, ethanol and water.
7. Dry.

(B) Amounts of Materials Used:

| Material | Range (% by weight) |
|---|---|
| Organic Solvent* | 58.50%–65.50% |
| Water | 5.06%–15.12% |
| SDBS | 0.20%–0.23% |
| CD | 0.76%–8.32% |
| Sodium Hydroxide | 2.68%–7.93% |
| EPI | 10.23%–15.96% |
| Diethylenetriamine | 4.52%–5.07% |
| Sodium Borohydride | 0.04% |
| Heating Time | 3–6 Hrs. |

*Examples of suitable organic solvents include, but are not limited to, toluene, benzene or hexane.

The invention has been described in an illustrative manner, and it is to be understood the terminology used is intended to be in the nature of description rather than of limitation.

Obviously many modifications and variations of the present invention are possible in light of the above teachings. Therefore, it is to be understood that within the scope of the appended claims, the invention may be practiced otherwise than as specifically described.

We claim:

1. A pharmaceutical formulation comprises a polymeric resin having bile acid binding properties selected from the group consisting of cholestyramine and colestipol in combination with at least one entrapped bile binding material for enhancing the bile acid binding affinity and/or capacity of the formulation.

2. The formulation of claim 1 wherein the bile binding material is selected from the group consisting of carbohydrates which bind bile acids, lipids which bind bile acids, proteins and proteinaceous materials which bind bile acids, and antibodies and albumins which bind bile acids.

3. The formulation of claim 1 wherein the bile binding material is a carbohydrate or carbohydrate fragment having an affinity for bile acid.

4. The formulation of claim 3 wherein the carbohydrate is a cyclodextrin selected from α-cyclodextrin, β-cyclodextrin and γ-cyclodextrin.

5. The formulation of claim 3 wherein the carbohydrate is a cyclodextrin derivative selected from the group consisting of β-cyclodextrin, 2-hydroxypropyl-β-cyclodextrin, 3-hydroxypropyl-β-cyclodextrin, 2,3-dihydroxypropyl-β-cyclodextrin, hydroxyethyl-β-cyclodextrin, and heptakis (2,6-di-O-methyl)-β-cyclodextrin.

6. The formulation of claim 1 wherein the bile binding material is present in an amount equal to from 10% to 50% by weight of the formulation.

7. A method for reducing cholesterol levels in a patient in need thereof which comprises administering to said patient an effective amount of a polymer resin capable of binding bile acids selected from the group consisting of cholestyramine and colestipol in combination with one or more entrapped bile binding material for reducing the cholesterol levels of the patient.

8. The method of claim 7 wherein the bile binding material is selected from the group consisting of carbohydrates which bind bile acids, lipids which bind bile acids, proteins and proteinaceous materials which bind bile acids, and antibodies and albumins which bind bile acids.

9. A process for preparing an improved pharmaceutical formulation by incorporating or diffusing at least one bile binding material into a polymeric resin capable of binding bile acids selected from the group consisting of cholestyramine and colestipol and subsequently retaining the bile binding material within the resin.

10. A process as set forth in claim 9 wherein the bile binding material is a binding carbohydrate, protein or lipid material or fragment or derivative thereof, said process being further defined as combining styrene, divinyl benzene, catalyst, and a cyclodextrin in water and forming an emulsion, heating the mixture to 85° C. until polymerization is complete, followed by swelling the resin in ether and reacting with chloromethyl ether at 0° C., then swelling in toluene and reacting with trimethylamine at 85° C.

11. The process of claim 9 wherein chloromethyl styrene and divinyl benzene are added in the presence of a catalyst to accelerate polymerization, adding water to form an emulsion, heating to 85° C. until polymerization is complete, followed by swelling the resin in toluene and reacting with trimethylamine.

12. The process of claim 10 wherein chloromethylated polystyrene is swelled in toluene, heated gradually, and reacted with trimethylamine.

13. The process of claim 10 wherein water is excluded from the formulation.

14. A process for preparing an improved pharmaceutical formulation by incorporating or diffusing at least one bile binding material into a polymeric resin capable of binding bile acids selected from the group consisting of cholestyramine and colestipol and subsequently retaining the bile binding material within the resin by the steps of swelling the resin in a solvent medium, mixing the resultant resin with the bile binding material and drying the mixture thereby shrinking the resin and entrapping therein the bile binding material.

15. The process of claim 14 wherein the alkali metal salt of an alkylbenzene-sulfonic acid is sodium dodecylbenzenesulfonate, the polyethylenepolyamine is diethylenetriamine and the cross-linking agent is epichlorohydrin.

16. The process of claim 14 wherein a second addition of a cross-linking agent is added following addition of the diethylenetriamine.

* * * * *